(12) United States Patent
Chen

(10) Patent No.: US 8,219,186 B2
(45) Date of Patent: Jul. 10, 2012

(54) NON-INVASIVE SYSTEM AND METHOD FOR SCANNING THE HEART

(76) Inventor: Guangren Chen, Palm Harbor, FL (US)

( * ) Notice: Subject to any disclaimer, the term of this patent is extended or adjusted under 35 U.S.C. 154(b) by 737 days.

(21) Appl. No.: 12/398,759

(22) Filed: Mar. 5, 2009

(65) Prior Publication Data

US 2010/0228138 A1 Sep. 9, 2010

(51) Int. Cl.
*A61B 5/0464* (2006.01)
*A61B 5/0402* (2006.01)

(52) U.S. Cl. .................. 600/518; 607/9; 607/4; 607/3; 600/509

(58) Field of Classification Search ............... 607/9, 3; 600/509
See application file for complete search history.

(56) References Cited

U.S. PATENT DOCUMENTS 5,871,507 A * 2/1999 Obel et al. ............... 607/9
2009/0259266 A1* 10/2009 Zhang et al. ............. 607/3

OTHER PUBLICATIONS

Acharya et al: "Cardiac Health Diagnosis using Wavelet Transformation and Phase Space Pilots" Proceedings of the 2005 IEEE Engineering in Medicine and Biology 27th Annual Conference, Jan. 1, 2005, pp. 3868-3871.*

Ana Gavrovska et al: "PVC Scalogram Detection using Neural Network" 9th Symposium on Neural Network Applications on Electrical Engineering, Neural 2008, Sep. 25, 2008, pp. 161-164.*

Ghosh D et al: "Wavelet Aided SVM analysis of ECG signals for Cardiac Abnormality Detection" IEEE INDICON 2005 Conference, Dec. 11, 2005, pp. 9-13.*

* cited by examiner

*Primary Examiner* — Carl H. Layno
*Assistant Examiner* — Jon-Eric C. Morales
(74) *Attorney, Agent, or Firm* — Law Office of Andra Vaccaro

(57) ABSTRACT

A non-invasive system and method of diagnosing and predicting cardiac disease in a patient's heart is disclosed that comprises a microprocessor which contains a signal processor and a pattern recognition processor; detect the electrophysiological signals of the heart whereby the signals are processed to create a pattern that represents the patient's heart. The pattern may be further processed by repeatedly comparing it to patterns stored within the pattern recognition processor whereby certain coronary diseases such as myocardial ischemia in the patient's heart may be diagnosed. During each heartbeat, at least a million different electrical signals are collected and the results of test are displayed on a screen. The results may include the diagnosis, computer generated image of the patient's heart identifying areas of any cardiac disease that has been detected and/or a two dimensional non-linear waveform representing the electrophysiological signals of the patient's heart. In a further embodiment, the system will also generate ECG waveforms.

27 Claims, 4 Drawing Sheets

NON-INVASIVE SYSTEM AND METHOD FOR SCANNING THE HEART

FIELD OF THE INVENTION

The present invention relates to a medical apparatus for scanning the heart to locate and detect heart malfunctions, vascular and nonvascular plaque and ischemia.

BACKGROUND OF THE INVENTION

Heart disease is one of the leading causes of death for both men and women throughout the world. According to the American Heart Association, an estimated one in three adults (80.7 million) have one or more types of cardiovascular disease of whom 38.2 million are estimated to be age 60 or older. Worldwide, coronary heart disease kills more than 7 million people each year. The United States Center for Disease Control (CDC) estimates that 47% of all cardiac deaths in the United States occur before emergency services are received or before the patient can be transported to a hospital.

In addition, in patients having coronary arterial disease, only approximately 40% experience symptoms such as angina, chest pain, shortness of breath, and light headedness. However, when an ECG (electrocardiogram) is taken of the patient's heart, many do not show a positive change in the current resting ECG, thus making it extremely difficult to identify if there is a level of myocardial ischemia (restriction of blood flow to the heart) present. According to the American Heart Association, at present, approximately 67% of all coronary arterial diseases are correlated to some degree of myocardial ischemia. Further, over 60% of patients with coronary arterial disease may not feel the symptoms of myocardial ischemia (i.e. they are asymptomatic) such that they do not visit their physician or clinic. 50 percent of men and 64 percent of women who died suddenly of coronary heart disease had no previous symptoms of this disease. This year an estimated 770,000 Americans will have a new coronary attack and about 430,000 will have a recurrent attack. It is estimated that an additional 190,000 silent first heart attacks occur each year. (NHLBI: Based on unpublished data from the ARIC and CHS studies.)

Cardiovascular testing represents an integral component of care for at-risk patients, both at the diagnostic stage and during patient care in a medical facility. According to data obtained from the Centers for Disease Control and Prevention's Annual National Hospital Discharge Survey, approximately 4.3 million patients were discharged from a hospital with a diagnosis of heart disease in 2006. In addition to the approximately 4.3 million patients discharged from a hospital with a diagnosis of heart disease in 2006, another approximately 15.3 million individuals received an ECG test in an ambulatory emergency clinic or hospital emergency department. Physicians also had approximately 23.7 million individuals tested with an ECG monitor and another approximately 2.1 million individuals received an ECG test in an outpatient care setting such as a cardiac rehabilitation center, according to the Centers for Disease Control and Prevention.

The number of heart related testing is expected to increase in tandem with the aging of the population, both at the diagnostic stage and during acute care. Trends toward preventive care and maintenance will also mean that more individuals diagnosed as high risk for a cardiac condition will receive more routine tests to monitor the progress of the condition. These trends, in tandem with the push to shorten hospital stays, have created an impetus to identify risks earlier in pre-symptomatic patients at the physician or clinic level and to treat recovering cardiac patients in cardiac rehabilitation centers.

Currently there are many tests that are used in connection with cardiovascular conditions. One common test that is performed is an angiogram which requires that a catheter be fed through an artery or vein into the area to be studied through which a dye is injected to make the blood flowing inside the blood vessels visible on an x-ray. An angiogram can show if coronary artery disease is present and how severe it is. However, angiograms are invasive, expensive and dangerous to perform.

Another test that is commonly performed is the non-invasive ECG. Current ECG technology detects approximately 1000 electrical impulses generated by the heart during each heart beat via skin electrodes and processes the impulses over time to create a one dimensional waveform that represents the heart. Specifically, the ECG breaks down each heartbeat into a series of three distinct electrical waves: the P wave, the QRS complex and the T wave. The P wave represents the activity in the heart's upper chambers while the QRST complex and T wave represent the activity in the lower chambers.

During an ECG, electrodes are placed on different sides of the heart to measure the activity of different parts of the heart muscle. The ECG displays the voltage between different pairs of these electrodes, and the muscle activity that they measure, from different directions, also understood as vectors. The ECG waveform indicates the overall rhythm of the heart and weaknesses in different parts of the heart muscle. It can measure and detect abnormal rhythms caused by damage to the conductive tissue that carries electrical signals, or abnormal rhythms caused by levels of dissolved salts (electrolytes), such as potassium, that are too high or low. While an ECG can assist in identifying damaged heart muscle, it can only identify damage to muscle in certain areas of the heart. Further, it cannot reliably measure the pumping ability of the heart.

Many people with coronary artery disease, heart valve disease or heart muscle disease will eventually show abnormal ECG readings. However, abnormalities that occur may not show up. Because it is very common to see this false-negative result (e.g., the EKG does not find the damage or abnormality that is really present), a normal ECG is not enough to rule out suspected heart disease.

SUMMARY OF THE PREFERRED EMBODIMENTS

The present invention is a system and method used to identify certain coronary diseases and more specifically, myocardial ischemia. In a preferred embodiment of the present invention, the system and method incorporates at least two dimensional mapping of the heart by continuously multiplexing the signals received from each of the ten surface electrodes during each heart beat. However, any other device that is capable of sensing and sending electrical signals other than electrodes can be used.

The system and method processes the signal received from each electrode on a beat-by-beat basis. During the initial processing, the amplitude, timing and frequency of these signals are measured. The processor then processes this information through triangulation to find the location and approximate magnitude of one or more compromised vascular situations if they are present.

More specifically, the preferred system of the present invention comprises a signal processor and a pattern recognition processor which process signals obtained by an electrical sensing device. In a preferred embodiment and method of the present invention, the sensing device may be electrodes or a wand or some other electrical device known in the art which can detect electrical signals which are processed by the signal processor to create a waveform pattern that represents the patient's heart. In a preferred embodiment, that waveform pattern is further processed by repeatedly comparing it to patterns stored within the pattern recognition processor. The patterns that are stored represent certain coronary diseases for which patterns have been obtained through medical research of patients having certain coronary diseases as confirmed by at least one test. In this manner diseases such as myocardial ischemia in the patient's heart and the presence of vascular and non-vascular plaque may be diagnosed. In an embodiment of the present invention, the pattern of the electrical activity that is detected is at a myocardial cellular level. In a preferred embodiment, the signal processor continuously multiplexes the electrical impulses to obtain readings from different areas of the patient's heart. During each heartbeat, at least a million different electrical impulses are collected.

In a preferred embodiment, a screen is provided onto which the diagnosis is displayed. In a further embodiment, the display contains a computer generated image of the patient's heart identifying areas of any coronary disease that has been detected. In yet another embodiment a two dimensional waveform representing the electrical impulses of the patient's heart can be shown. In a further embodiment, the system can also generate ECG waveforms. In a preferred embodiment the pattern recognition processor further comprises a database of patterns representing patients who have had at least some form of myocardial ischemia, such that when a patient's pattern is created by the signal processor, the pattern is compared to other patterns in the database. The pattern recognition processor further comprises a database of patterns representing patients who have had at least some form of cardiac disease and patients who have no cardiac disease, such that when a patient's pattern is created by the signal processor, the pattern is compared to other patterns in the database. In a preferred embodiment, the pattern recognition processor adds the pattern of any patients that are tested that have any form of coronary disease into its database.

In a preferred method of the present invention which tests a patient for certain coronary disease, the method comprises the steps of obtaining the electrical impulses of the heart from a means for sensing the electrical impulses; processing and multiplexing the electrical impulses received from each of means for sensing to create a two dimensional waveform; processing the two dimensional waveform to create a pattern; comparing the waveform to other waveforms contained within a database in a microprocessor which is comprised of patterns for patients that have certain coronary disease; whereby when the patient's waveform compares to one or more waveforms contained within the database, coronary disease may be detected.

In a preferred method, the results of the test are displayed on a screen. In a preferred method, the two dimensional waveform that is created is displayed. In a preferred method of the present invention, at least one million electrical impulses are processed during each heartbeat to create the two dimensional waveform. In a further preferred method of the present invention, the step of processing and multiplexing the electrical impulses received from each of the electrodes also creates an ECG waveform. In yet another method of the present invention, the results of the test will be displayed on a screen, such that either a computer generated image of the patient's heart in which any areas of Myocardial ischemia will be identified or a two dimensional waveform representing the electrical impulses of the patient's myocardium will be shown, or both.

Another preferred method of the present invention obtains at least two dimensional information about at least one area of a patient's heart. In this preferred method, the method comprises the steps of obtaining a cardiac electrophysiology signal from electrodes placed on the patient's body; continuously scanning the patient's heart beat by beat to create a two dimensional graph representing the electrophysiology of the patients heart; and identifying at least one location in the patient's heart where there is a change in the electrophysiology. In a preferred method, the step of identifying at least one location in the patient's heart, comprises processing the electrophysiology signal by comparing it to quantitative medical informatics contained in a computer communicating with the electrodes. In yet another preferred method of the present invention, the method further comprises the steps of identifying on the graph the peak edges which surround the PQRST locations of a patient's heart, assigning an energy level to each of the identified locations using the electrophysiology signals beat by beat. In a preferred method, the method further comprises the step of assigning a color scale to represent the energy levels in the identified locations and/or using the electrophysiology signal of the heart so as to create a colorized waveform wherein each color represents the energy level on a beat by beat basis of the area in the myocardium.

BRIEF DESCRIPTION OF THE DRAWINGS

The detailed description of the invention will be made with reference to the accompanying drawings, where like numerals refer to like parts and in which.

DETAILED DESCRIPTION OF THE PREFERRED EMBODIMENTS

In the following descriptions of the invention, terms such as "top," "bottom," "left," "right" and the like are used herein merely for ease of description and refer to the orientation of the components as shown in the Figures.

Generally, the present invention may be briefly described as follows. In the human heart, the heartbeat is regulated by the pneumogastric (vagus) and sympathetic nerves which create electrical impulses (physiology) which regulate the blood flow through the body. The heart is a three-dimensional object with time being the fourth dimension.

It is known that the heart has three distinct waves—the P wave, the QRS complex and the T wave. The P wave represents the activity in the heart's upper chambers while the QRST complex and T wave represent the activity in the lower chambers where the myocardium is located. The myocardium of the heart has 10 layers, where the direction, speed and strength of the electrical impulses are different. Since the myocardial layers have over one hundred million myocardial cells there are millions of impulses that can be detected.

Figure 1:
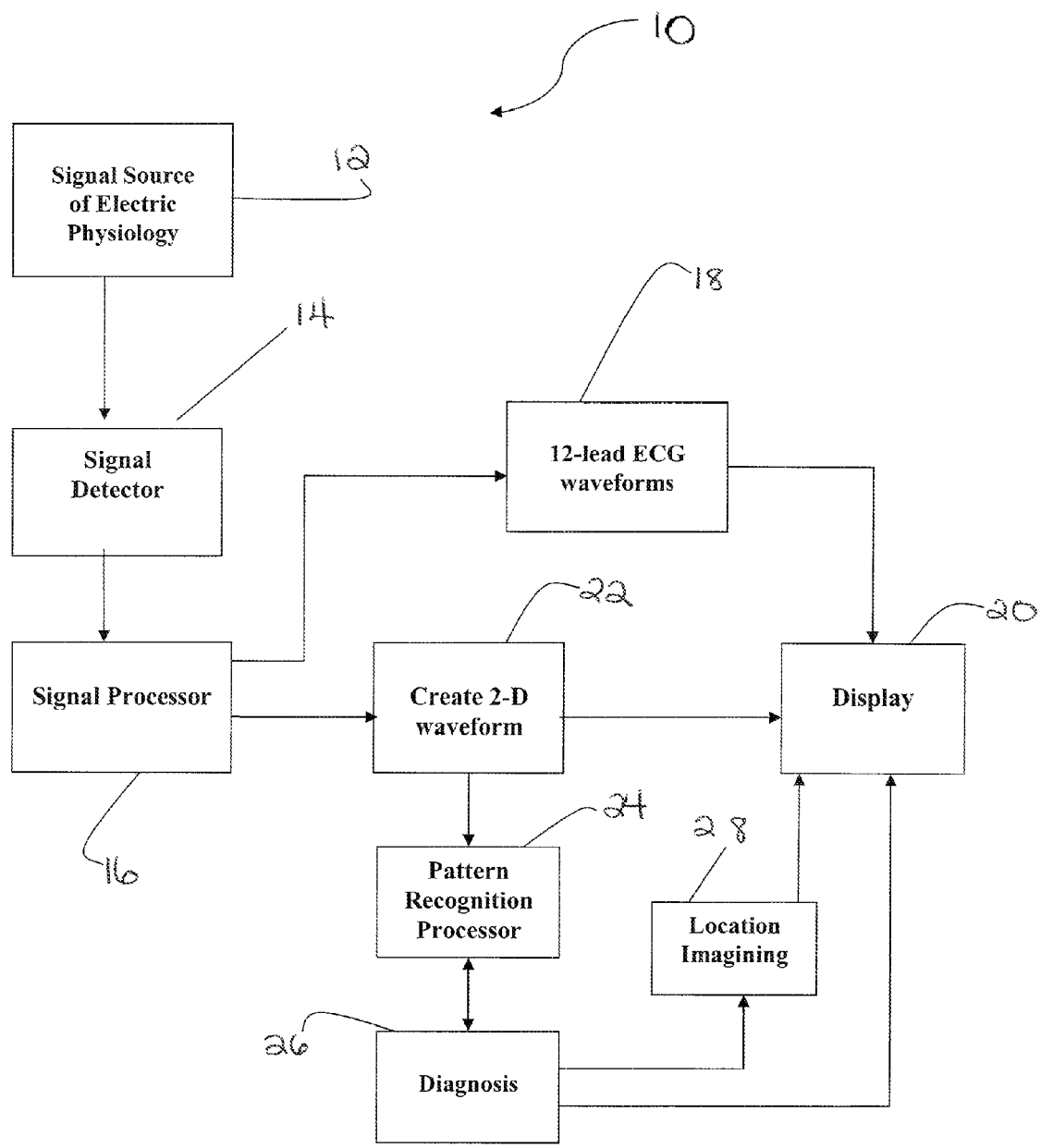
FIG. 1 is a block diagram of the system of the present invention.

Referring first to FIG. 1, in a preferred embodiment of the present invention, the system 10 detects at least 1 million impulses sent by the heart during each heartbeat. However, more or less impulses may be obtained for processing with suitable modifications of the system.

The impulses are gathered by the signal source 12. In a preferred embodiment the signal source is a plurality of electrodes, which are placed on certain areas of the patient's body to measure the activity of different parts of the heart muscle. In a preferred embodiment, the electrodes are placed as follows:

Lead I: LA-RA: Left foreleg (left arm) electrode (+) placed just below the point of the elbow on the back of the left forearm—right foreleg (right arm) electrode (−) placed just below the point of the elbow on the back of the right arm.

Lead II: LL-LA: Left hindleg (left leg) electrode (+) placed on the loose skin of the left stifle in the region of the patella— left foreleg (left arm) electrode (−) placed just below the point of the elbow on the back of the left arm.

Lead III: LL-RA: Left hindleg (left leg) electrode (+) placed on the loose skin of the left stifle in the region of the patella—right foreleg (right arm) electrode (−) placed just below the point of the elbow on the back of the right arm.

aVR: RA-CT: Right foreleg (right arm) electrode (+) placed just below the point of the elbow on the back of the right forearm—the electrical center of the heart or central terminal x3/2; left foreleg and left rear leg (−)

aVL: LA-CT: Left Foreleg (left arm) electrode (+) placed just below the point of the elbow on the back of the left forearm—the electrical center of the heart or central terminal x3/2; right foreleg and left rear leg (−)

aVF: LL-CT: Left hindleg (left leg) electrode (+) placed on the loose skin at the left stifle in the region of the patella— the electrical center of the heart or central terminal x3/2; right foreleg and left foreleg (−)

CV6LL: VI-CT: VI electrode (+) placed in the $6^{th}$ intercostals space on the left side of the thorax along a lone parallel to the level of the point of the elbow—the electrical center of the heart (central terminal)

CV6LU: V2-CT: V2 electrode (+) placed in the $6^{th}$ intercostals space on the left side of the thorax along a lone parallel to the level of the point of the shoulder—the electrical center of the heart (central terminal)

V10: V3-CT: V3 electrode (+) placed over the dorsal thoracic spine of T7 at the withers electrical center of the heart. The dorsal spine of T7 is located on a line encircling the chest in the $6^{th}$ intercostals space (center terminal)

CV6RL: V4-CT: V4 electrode (+) placed in the $6^{th}$ intercostals space of the right side of the thorax along a line parallel to the level of the point of the elbow—the electrical center of the heart (central terminal)

CV6RU: V5-CT: V5 electrode (+) placed in the $6^{th}$ intercostal space on the right side of the thorax along a line parallel to the level of the point of the shoulder—the electrical center of the heart (central terminal)

Base-Apex: LA-RA: Left foreleg (left arm) electrode (+) placed in the $6^{th}$ intercostals space on the left side of the thorax along a line parallel to the level of the point of the elbow—right foreleg (right arm) electrode (+) placed on the top of the right scapular spine or ever the right jugular furrow.

Alternatively, instead of using electrodes, a signal detector such as a wand is passed over the patient's body in the same locations as the electrodes, although any signal source that is capable of detecting the electric physiological impulses of the heart may be used with suitable alterations of the processing.

In a preferred embodiment, the electrical impulses detected by the electrodes are amplified by a signal detector 14. In a preferred embodiment the amplification is done by an analog to digital and a digital to analog processor which reduce the frequency disturbances and any myo-electrical noise. Because there are numerous electrical impulses received, many of the signals will overlay one another or become integrated.

The amplified signals are then sent from the signal detector 14 to the signal processor 16. The signal processor separates the overlaid and integrated signals and also separates the signals into their various components—frequency, amplitude, time and location. The signal processor 16 then sends the processed signals to an ECG processor 18 and a 2D waveform creator 22. The ECG processor 18, processes the signals through well known techniques to obtain the PQRST waveforms which are then displayed on display 20.

The 2D waveform creator 18 takes the various processed signals representing the four dimensions of the heart and combines them together to create a 2D waveform representative of the energy and frequency of the blood flowing through the heart which is then displayed on display 20.

In order to obtain the 2D waveform, the wavelengths of each signal are processed by a continuous wavelet transform (CWT) so that the high-frequency signals are displayed on the low scale and the low-frequency signals are displayed in high-scale. The CWT uses plethysmography and minimum variance methods and Eigen analysis frequency estimation. The 2D signals represent the amount that the intensity values at at least 5 locations in an area of the heart varies over time. Specifically the 2D image is a plot of the frequency, amplitude and time as a fundamental sine wave as they are formed by rotating the vectors formed by combinations of the electronic impulses received from the signal source. To create the 2D waveform, the time-domain signal is processed through a number of filters to obtain a waveform in the time and frequency domains. This series of filters have basic features, such that if the center frequency is higher, its bandwidth is greater, while if center frequency is lower, its bandwidth is narrower.

In a preferred system and method of the present invention, there are at least two possible ways of displaying the 2D waveform, one where the X-axis represents time; the Y-axis represents frequency (the number of signals); and the Z axis represents amplitude (energy of the signal to identify the origination location of the signal); in another display the X-axis represents time; the Y axis represents amplitude; and the Z-axis represents frequency.

Figure 3:
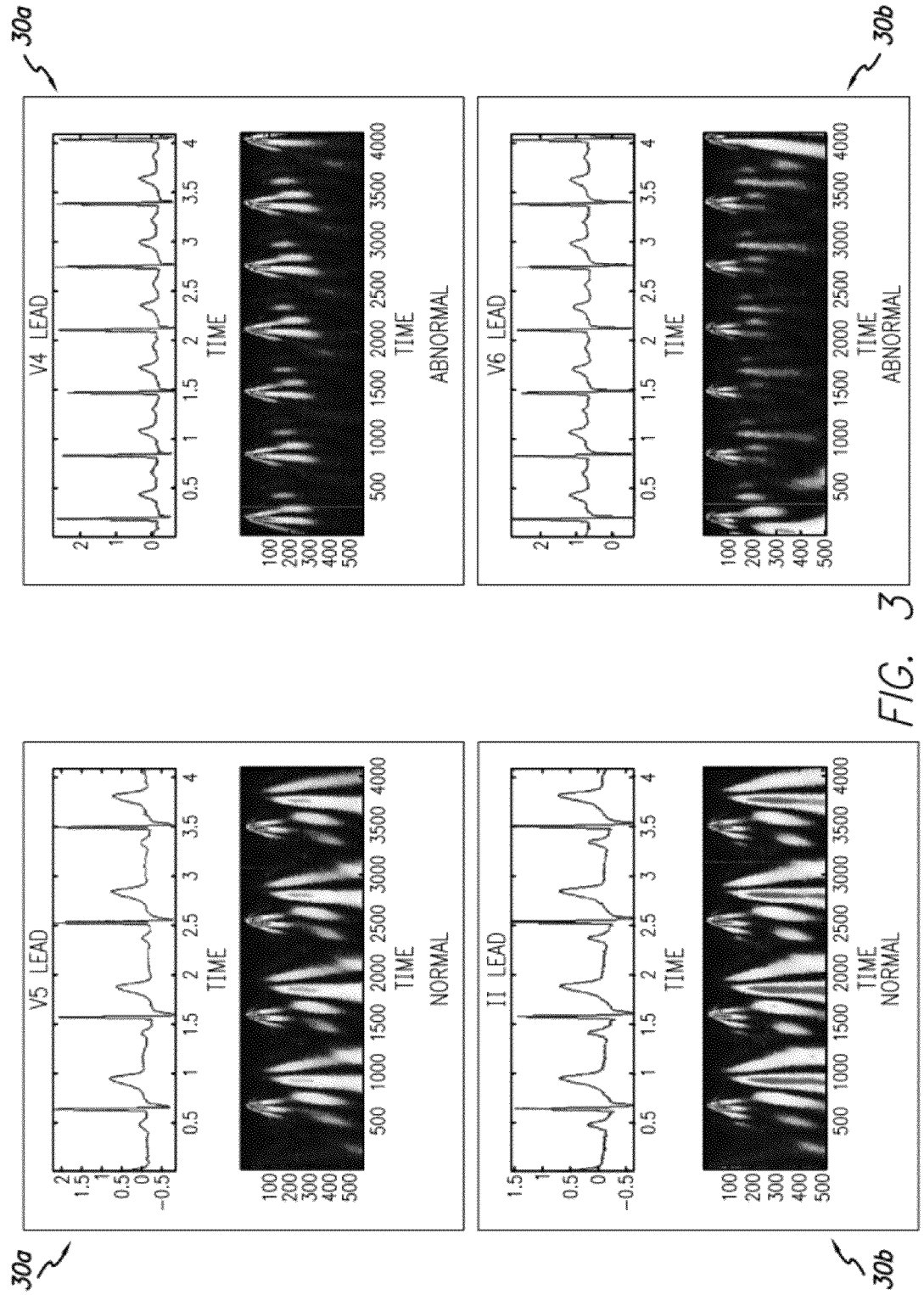
FIG. 3 are examples of color waveforms of heart scans created by the system and method of the present invention, in which the left waveforms are for normal hearts (i.e. hearts that do not have coronary diseases) and the right waveforms are for hearts that have coronary disease.

Referring also to FIG. 3, in a preferred system and method of the present invention, a color scale can be selected so that the 2D waveform creator 22 signal will create a waveform having different colors representative of different parts of the heart function. Specifically, the colors will represent the energy levels in various locations on a beat by beat basis of an area such as the myocardium such as is shown in the image in FIG. 3. Different colors represent the QRS and the T functions of the heart. At the left side of FIG. 3, 2D color waveforms 30a and 30b of normal hearts are shown. At the left of FIG. 3, 2D color waveforms 31a and 30b of hearts having myocardial ischemia are shown.

The 2D waveform is sent to the pattern recognition processor 24 where it is compared to patterns contained in a database representing certain coronary diseases. Specifically, in a preferred embodiment, the pattern recognition processor 24 contains a database of patterns representing at least 50,000 patients who have been diagnosed as having various coronary diseases and whose diagnosis has been confirmed by other methods such as angiograms and the like. In a preferred embodiment, the pattern recognition database is repeatedly updated by adding the patterns of each new patient for whom some form of coronary disease has been diagnosed.

In a preferred embodiment of the present invention, the pattern recognition processor 24 compares the waveforms created by the 2D processor with the waveforms in its database using triangulation or other well known waveform comparison techniques. When a match is found, it alerts the diagnosis database 26 which contains a list of known diagnosis corresponding to the waveforms in the pattern recognition database. The diagnosis database 26, selects the diagnosis from its database that correlates to the waveform pattern that matches the patient's waveform and sends it to the display 20. In addition, in some embodiments of the system and method of the present invention, the diagnosis is also sent to an imaging database 28 which selects an image that closely resembles the type and location of the disease and sends the image to the display 20.

Figure 4:
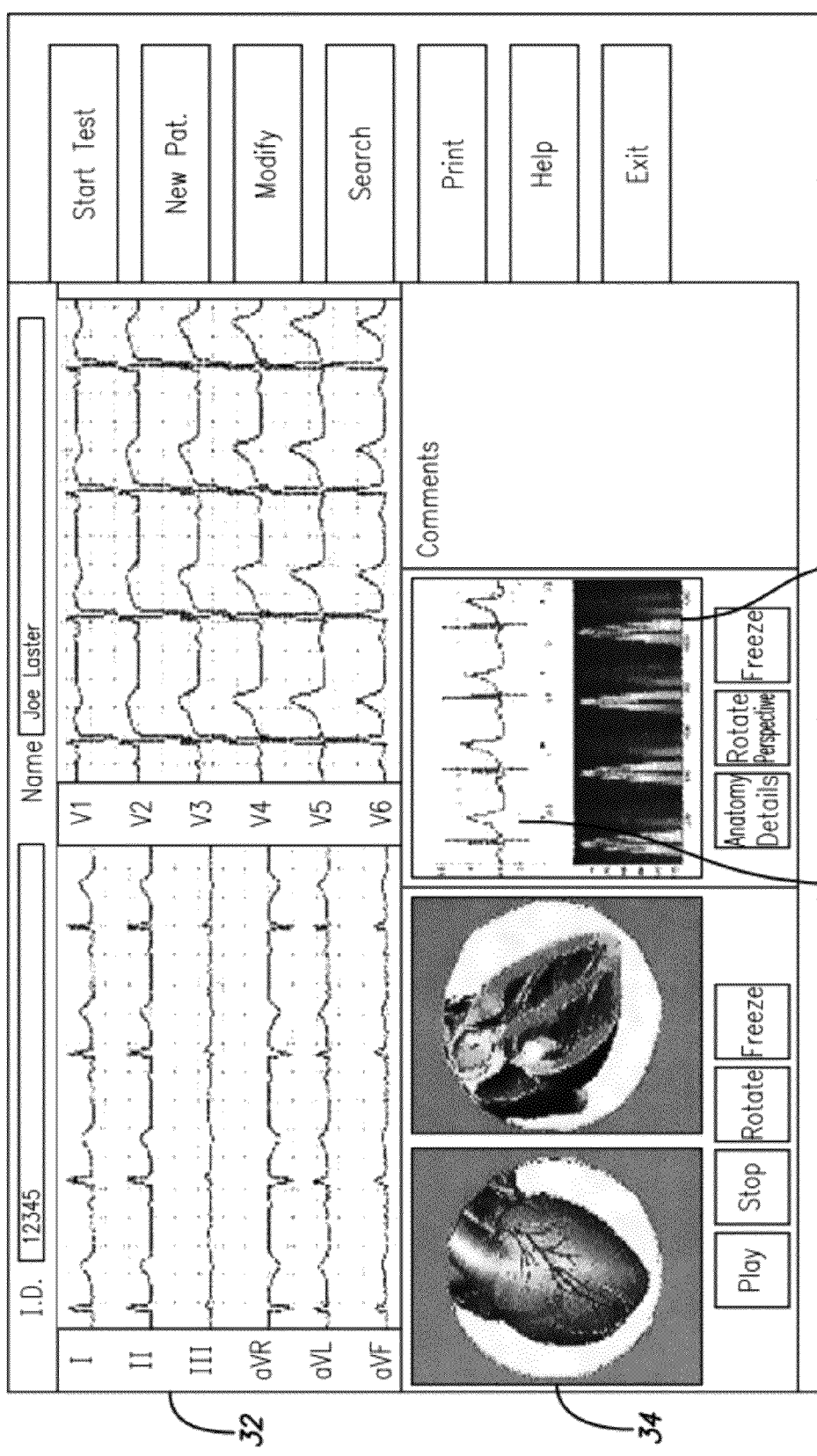
FIG. 4 is an example of the screen displaying results obtained using the system and method of the present invention.

In FIG. 4, a typical display 20 having all of the information that is available from the system and method of the present invention is shown. Specifically, in a preferred embodiment of the display 20, the ECG waveforms 32 are shown on the top showing the 12 vectors commonly shown during a usual ECG test. At the bottom of the screen, image 34 of a heart that closely resembles the type and location of the disease in a patient that has been scanned that has that disease in the same location is shown. Next to image 34, a 2D waveform 36 of the time, frequency and amplitude of the patient that has been scanned is shown, as is the 2D colorized waveform 38 of that patient.

Figure 2:
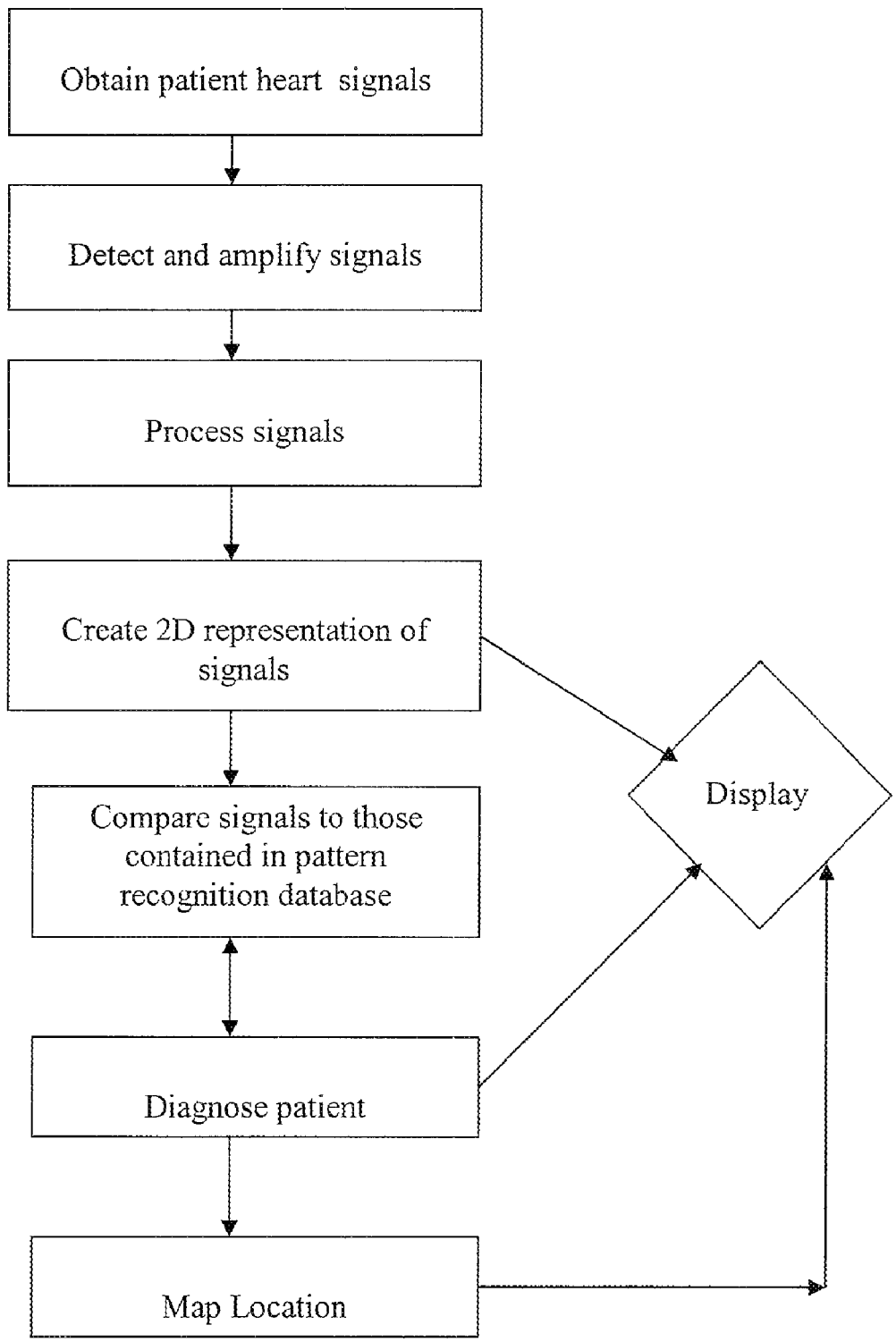
FIG. 2 is a flow chart showing a preferred method of the present invention.

Referring next to FIG. 2, a flow chart of a preferred method of the present invention is shown. Specifically, once a signal is obtained reflecting the electrical physiological activity of the patient's heart from electrodes placed on and around the heart in accordance with well known principles or by a wand scanning the patients heart or by any other device capable of accurately detecting the signals, the signals are communicated to a signal detected where they are processed so that the signals are amplified. In a preferred method, the signals go through an analog to digital transformer and then are transformed back into analog by a digital to analog transformer. However, any processor or transformer that is capable of amplifying the signal may be used. The amplified signal then is further processed for noise reduction and to determine the frequency, amplitude and timing of each signal received for each heartbeat. In a preferred method of the present invention, this is accomplished by using sin and cosine transformations well known in the art. A minimum of 1 million signals representative of the heart are received during one heartbeat. However, more or less signals may be utilized with suitable modifications of the processing. The processed signal is then transformed into a two dimensional signal.

The 2D signal is then processed by a pattern recognition processor which contains a database of patterns that are representative of various abnormalities known to appear in the heart such as, but not limited to, plaque, myocardial ischemia and other abnormalities. In the pattern recognition processor, the pattern of the particular patient being tested is compared using known methods of wave comparison to determine whether the pattern compares to any patterns in the database. If an abnormality is detected, the location of the abnormality is determined based upon the data in the diagnosis database and is mapped on a picture of a heart that also exists in the database and then it is displayed on the display. At the same time, the system will print out in text the type and location of the abnormality as well as the diagnosis based from the database containing diagnosis. At the same time if the patient is determined to have an abnormality, the pattern from that patient is added to the database as another example of a pattern representative of a specific type of abnormality to build up the data in the database.

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein. The embodiments and methods described above are exemplary embodiments and methods of the present invention. Those skilled in the art may now make numerous uses of, and departures from, the above-described embodiments and methods without departing from the inventive concepts disclosed herein. Thus, the construction of the embodiments and the steps of the methods disclosed herein are not limitations of the invention. Accordingly, the present invention is to be defined solely by the scope of the following claims.

What is claimed is:

1. A non-invasive system for diagnosing and predicting cardiac events and vascular disease in a patient's heart, the system comprising:
   a microprocessor comprising a signal processor and a pattern recognition processor;
   non-invasive means for repeatedly obtaining the electrophysiological signals of the patient's heart, and communicating them to the microprocessor; for
   processing by the signal processor to create a non-linear waveform pattern representative of the patient's heart, whereby that pattern is repeatedly compared to patterns stored within the pattern recognition processor to diagnose whether there has been or whether there might be future, cardiac events and/or vascular disease in the patient's heart.

2. The non-invasive system of claim 1 wherein the pattern representative of the patient's heart is of the myocardial cell's electrical activity at a sub-cellular level.

3. The non-invasive system of claim 1 wherein the signal processor continuously multiplexes the electrophysiological signals received from the means for sampling so as to ascertain readings from different locations in the patient's heart.

4. The non-invasive system of claim 1 further comprising a screen onto which the diagnostic reference is displayed.

5. The non-invasive system of claim 1 further comprising a display onto which a two dimensional atlas and quantitative data index of the patient's heart will be shown identifying any areas of Myocardial ischemia, injury, necrosis and infarction or any other cardiac disease.

6. The non-invasive system of claim 1 further comprising a display onto which a two dimensional waveform representing the electrophysiological signals of the patient's myocardium will be shown.

7. The non-invasive system of claim 1 wherein the microprocessor further comprising a processor for generating ECG waveforms.

8. The non-invasive system of claim 1 wherein the pattern recognition processor further comprises means for creating a database of patterns representing patients who have had at least some form of cardiac disease, such that when a patient's pattern is created by the signal processor, the pattern is compared to other patterns in the database.

9. The non-invasive system of claim 1 wherein the pattern recognition processor further comprises a database of patterns representing patients who have had at least some form of cardiac or vascular disease and patients who have no cardiac or vascular disease, such that when a patient's pattern is created by the signal processor, the pattern is compared to other patterns in the database to diagnose whether any cardiac and/or vascular disease is present in the patient's heart and to predict whether the patient is likely to have any cardiac event.

10. The non-invasive system of claim 1 wherein at least a million electrophysiological signals are collected during a predetermined period of time.

11. The non-invasive system of claim 1 wherein the microprocessor has an input mechanism for inputting data regarding each patient that is tested.

12. The non-invasive system of claim 1 wherein the pattern recognition processor enters into its database patterns for any patients that are tested that have any form of myocardial ischemia, injury, necrosis and infarction or any other cardiac disease.

13. The non-invasive system of claim 1, wherein the means for conducting comprise electrodes containing microchips for communicating with the microprocessor.

14. A non-invasive method of testing a patient for certain cardiac disease, comprising the steps of:
repeatedly obtaining electrophysiological signals generated by the heart from a means for sensing the signals;
processing and multiplexing the electrophysiological signals received from the means for sensing to create a two dimensional non-linear waveform;
whereby comparing the two dimensional non-linear waveform to other waveforms contained within a database in a microprocessor which is comprised of waveforms of patients that have certain cardiac diseases and no cardiac disease such that a clinician can determine whether the patient has any cardiac disease.

15. The non-invasive method of claim 14, wherein when the test is completed, displaying the results of test on a screen.

16. The non-invasive method of claim 14, further comprising the steps of displaying the two dimensional non-linear waveform that is created.

17. The non-invasive method of claim 14, further comprising the steps of inputting information related to each patient prior to commencing each test.

18. The non-invasive method of claim 14, further comprising the steps of obtaining at least one million electrophysiological signals to create the two dimensional non-linear waveform.

19. The non-invasive method of claim 14 wherein the step of processing and multiplexing electrophysiological signals received from each of the electrodes also creates an ECG waveform.

20. The non-invasive method of claim 14 further comprising the steps of displaying on a screen a computer generated image of the patient's heart in which any areas of myocardial ischemia, injury, necrosis and infection or any other cardiac disease will be identified.

21. The non-invasive method of claim 14 further comprising the steps of displaying on a screen the nonlinear two dimensional waveform representing the electrophysiology signals of the patient's myocardium in the left and right ventricle.

22. A non-invasive method of obtaining at least two dimensional information about at least one area of a patient's heart, the method comprising the steps of:
repeatedly obtaining a cardiac electrophysiology signal from electrodes placed on the patient's body;
continuously scanning the patient's heart beat by beat to create a two dimensional non-linear graph representing the electrophysiology of the patient's heart; and
wherein changes in cardiac electrophysiology signal are detected continuously such that at least one location in the patient's heart where there is a change in electrophysiology is identified.

23. The non-invasive method of claim 22, wherein the step of identifying at least one location in the patient's heart, comprises processing the electrophysiology signal in multi-domains.

24. The non-invasive method of claim 22, further comprising the steps of identifying on the graph the peak edges which surround certain preselected locations of a patient's heart, and assigning an energy level to each of the identified locations beat by beat.

25. The non-invasive method of claim 24, wherein the energy levels are the energy levels of the myocardial cells in the left and the right ventricle.

26. The non-invasive method of claim 25, further comprising the step of assigning a color scale to represent the energy levels in the identified locations.

27. The non-invasive method of claim 22, further comprising the step of using the electrophysiology signal of the heart so as to create a colorized waveform wherein the density of each color represents the electropotential energy level in the left and right ventricle on a beat by beat basis.

* * * * *